United States Patent [19]

Hara

[11] 4,289,620
[45] Sep. 15, 1981

[54] HIGH PRESSURE GLASS COLUMN FOR HIGH PERFORMANCE LIQUID CHROMATOGRAPHY

[76] Inventor: Shoji Hara, 1618, Shiki, Shiki-shi, Saitama, Japan

[21] Appl. No.: 92,980

[22] Filed: Nov. 9, 1979

[30] Foreign Application Priority Data

Nov. 22, 1978 [JP] Japan .................. 53-143338

[51] Int. Cl.³ .................. C02F 1/68; G01N 31/06
[52] U.S. Cl. .................. 210/198.2; 55/386; 422/70
[58] Field of Search .................. 23/232 C; 422/70, 89, 422/101, 103; 210/31 C, 198.2; 55/386; 73/23, 23.1

[56] References Cited

U.S. PATENT DOCUMENTS

| | | | |
|---|---|---|---|
| 3,250,395 | 5/1966 | Blume | 422/70 |
| 3,474,908 | 10/1969 | Catravas | 210/198 C |
| 3,791,522 | 2/1974 | Eisenbeiss et al. | 219/198 C |
| 4,131,547 | 12/1978 | Michel et al. | 210/198 C |

OTHER PUBLICATIONS

Suoboda, Vratislav et al., Journal of Chromatography, 148 (1978), 75-77.

Primary Examiner—William F. Smith
Assistant Examiner—Chris Konkol
Attorney, Agent, or Firm—Oblon, Fisher, Spivak, McClelland & Maier

[57] ABSTRACT

An improved high pressure glass column for high performance liquid chromatography which comprises, both ends of the high pressure glass column on which flanges made of the same glass material are arranged, two column end fitting plugs which are made of a fluorine-contained resin and have a small bore for the effluent flow bored in their center, a piston part of a fitting plug inserted in the bore syringe part of the column end and a flange arranged to attach to the flange of the glass column tube, where the inside of the end of the piston part is formed with a conic shape and one or more narrow circled hollows are formed around the outlet of the piston part, two filters made of the fluorine-contained resin placed in between the both ends of the piston part of the fitting plug and the solvent material packed into the column, and two clips fitting and holding the two flanges of the column and the plugs.

5 Claims, 6 Drawing Figures

HIGH PRESSURE GLASS COLUMN FOR HIGH PERFORMANCE LIQUID CHROMATOGRAPHY

BACKGROUND OF THE INVENTION

This invention relates to the development of the high pressure glass column for high performance liquid chromatography.

Up to now, the stainless steel tube has been almost exclusively utilized for preparing a high pressure column in modern liquid chromatography. Although stainless steel is mechanically convenient material for designing and sealing up the end fitting of the high pressure column, it has some unfavorable features as follows: the packing material is not visible in the stainless steel tube, leading to difficulty in taking care of the packing materials and packing system during the operation; the column tube material itself is deteriorated by acid; and the inside wall of the tube is required to be polished up before use for reducing the unfavorable wall effect and for obtaining a high efficiency column.

As another alternative, a glass column tube has been proposed, because it is transparent permitting the sorbent packed in the column and the whole packing system to be visible, and the glass material itself is stable for acids and various chemicals.

However, the system for the design of the end fitting and sealing up of the column becomes difficult, because of the fragility of the glass material. Consequently, the end-fitting and sealing up-system of the column ends must be incorporated with some complex shock-absorbing mechanism such as an O-ring.

FIG. 1 shows an example of the column fitting system used for the glass column which has been conventionally available and indicates the cross section of one part of the column end. The end of the glass column tube 1 has a flange 2, and column fitting plug 4 which is inserted into the glass column tube 1 also has a flange 5. The narrow bore 3 for the effluent flow is provided in the center of the fitting plug 4. Between the two flanges 2 and 5, an O-ring is placed and the column fitting plug 4 and the column tube 1 are tightly screwed up by using the two male and female screws made of metal 7 and 8. A filter 9 is placed between the outlet of the column end fitting 4 and the packing material 10.

The complex structural mechanism of this system containing the male and female screws made of metal and the O-ring produces dead spaces in the inlet part of the column and unfavorable irregular eddy diffusion of the effluent takes place. Consequently, the eluent and the sample injected enter into the dead spaces and the column efficiency is decreased.

By the strong compression of the screws, the O-ring made of synthetic rubber or a fluorine-contained resin is often broken, leading to a leak of the effluent. As far as employing the O-ring in the column end fitting system, it is usually difficult to use the glass column for a high pressure of over 20 kg/cm$^2$. This means that the slurry packing procedure by using high pressure, which is required for obtaining a high efficiency column is not able to be applied for such a glass column tube.

As a result, the glass column has been utilized only for the limited case of academic research and the analytical work involving the use of a strong acidic eluent as the mobile phase, which does not allow the use of a stainless steel column tube.

The purpose of this invention is to prepare a high efficiency glass column which can be used under a high pressure. In order to achieve this, the design of the system for the high pressure sealing of the column end fitting was widely examined.

By reducing the complexity of the conventional glass column system, the dead space involved in the column end fitting plug will be decreased, and therefore, the simplification of the design for the column end-fitting system excluding the use of an O-ring as well as with a high pressure sealing mechanism was desired.

A new high pressure sealing system allowing the application of the slurry packing procedure, and a simple sealing structure with no O-ring, affording the minimum dead space, was studied. As a result, a high pressure-high efficiecy column incorporating the minimized dead space in the column end fitting was realized.

The other items intended for this invention will be described in the following.

SUMMARY OF THE INVENTION

For accomplishing the intention of this invention, the various designs of the end fitting plug for the high pressure column were broadly examined. Finally, it was found that a glass tube bearing up against the high pressure operation, in which the column end is diminished to a small bore syringe tube and then a flange made of the same glass material arranged on the end, is very suited for preparing the high pressure sealing system and is able to be utilized for the high speed run.

In the narrow bore syringe part of the column end, a piston part of the end fitting plug made of the polymer material which is less hard than the glass and is stable for acids, solvents and various chemicals is tightly inserted.

The column end fitting plug has a small bore in its center for the effluent flow. The outlet part of the end fitting plug has a specifically designed piston. The inside of the outlet of the piston is conically formed. Outside of the piston, one or more circled narrow hollows were also formed. The column end fitting plug has a flange in its middle part. The flange is tightly attached to the flange of the glass column tube by using clips.

Such a simple sealing up mechanism allows one to use the glass column under the high pressure of 50 to 150 kg/cm$^2$. In this instance, no leak of the solvent is observed. As the high pressure slurry packing procedure becomes applicable, the high efficiency glass column is able to be obtained.

DETAILED DESCRIPTION OF THE PREFERRED EMBODIMENTS OF THE INVENTION

In this section, the preferred embodiment of the invention is described according to the figures.

FIG. 2 shows the cross section of an upper part of the one column end.

FIG. 3 also shows the enlarged cross section of an upper inlet of the column inlet and arrows indicate the direction of the pushing force produced by the pressurized effluent flow.

Figure 1:
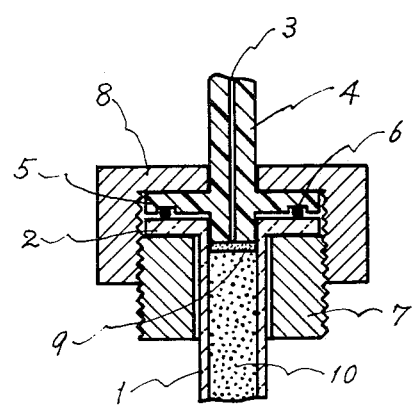
Figure 2:
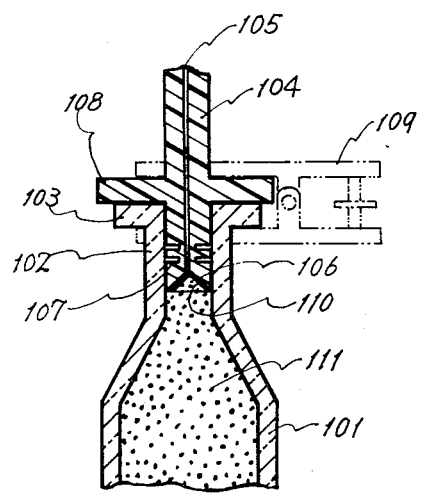
Figure 3:
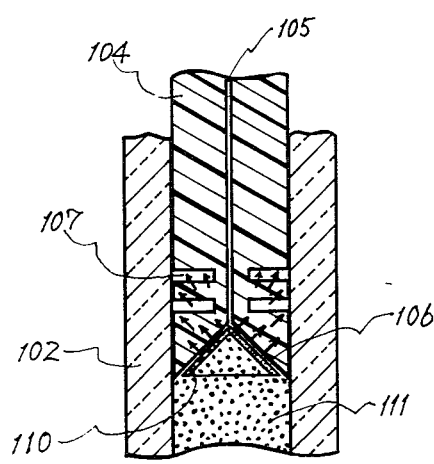
Figure 4:
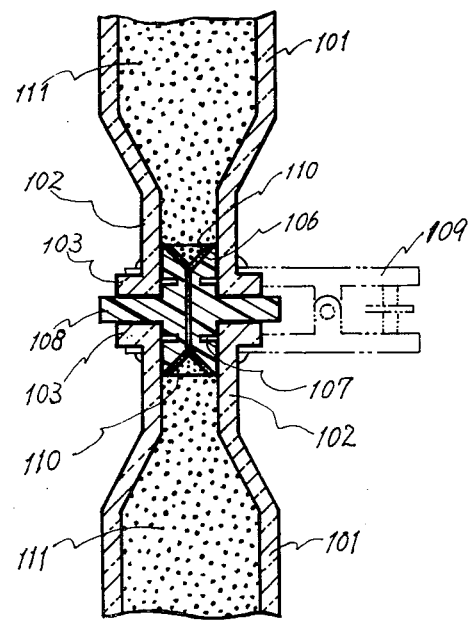
FIG. 4 shows the cross section of the two columns connected on line in a sequential series.

In the FIGS. 2 and 3, 101 indicates the main part of the high pressure glass column tube. The inner diameter of both ends of the column tube is diminished in a conical shape. The glass syringe tube 102 has a flange 103 made of the same glass material. The column end fitting plug 104 has a piston which is inserted tightly into the mouth of the column. The plug 104 is made of a material being stable against acids, solvents and various chemicals and being softer than glass material, for example, a synthetic rubber, a fluorine-contained resin and the like.

In the center of the column end fitting plug 104, the narrow bore 105 for the effluent flow is formed. The inner portion of the outlet of the fitting plug is formed with a conic shape which is indicated by 106. Around the outlet of the fitting plug 104, one or more narrow circled hollows 107 are formed.

In the middle of the fitting plug 104, the flange 108 is provided for attaching with the flange of the glass column end, 103. The two flanges 103 and 108 are tightly pressed together. The filter 110 (pore size of 5 micron, Daikin-Kogyo Co.) made of polytetrafluoroethylene is placed in between the outlet of the end fitting plug 104 and the sorbent 111 packed into the column.

The procedure for constructing the glass column described in this invention is as follows: the piston part of the column fitting plug 104 is inserted into the lower outlet of the high pressure glass tube 101, and the filter is placed on the outlet of the fitting plug. The column sorbent 111 is introduced through the upper outlet of the glass column tube and the sorbent bed is formed. In this case, high pressure slurry packing procedure is recommended.

The upper filter is placed on the sorbent bed and the piston part of the upper fitting plug 104 is inserted into the upper syringe tube of the glass column 101. The flange 103 provided by the glass column tube and the flange 108 provided by the column-end fitting plug are jointed together by the clip 109. The column for high pressure liquid chromatography is completed and now ready for use.

For separating each component in a given sample mixture, the effluent and then the sample solution are introduced into the head of the column through the small bore 105 of the column-end fitting plug by using a high pressure pumping device.

The conical hollow 106 provided inside of the plug piston outlet is pressed onto the inside wall of the column tube 102 and the mouth of the hollow 106 is opened by the pressurized eluent flow, while at the same time, the circular hollows formed around the outside of the piston of the column-end fitting plug shrink and the outlet of the fitting plug 104 compresses against the inside of the glass column tube 101. As a result, a leak of the effluent is prohibited.

The piston of the column-end fitting plug inserted into the glass column is tightly attached to the inside wall of the column and, therefore, only a clip is necessary for fitting and holding the two flanges of the column and the plug. When the given sample mixture is injected into the column, the constituents are separated with high resolution.

In this invention, the interdiameter of the column end is recommended to be 4–30 mm, preferably 4–10 mm and the like material for the fitting plug is recommended to be various fluorine-contained resins such as Teflon, Tefzel (du Pont) and the like.

The glass column tube developed here includes no O-ring and no metal screw. These specific features are different than the conventional glass column system having the O-ring and the screws for fitting. These characteristics of this invention provide a new mechanism for the construction of the high pressure glass column, leading one to prepare the high efficiency column by using a slurry packing device.

This system provides not only the high pressure sealing, but also minimizes unfavorable eddy diffusion by eliminating the void, which is always incorporated in the conventional glass column systems. Sample and effluent are introduced and distributed to the head of the column bed from the conical shaped outlet of the fitting plug. The irregular diffusion which has often taken place in the column-end fitting region is almost eliminated in this system. Consequently, the preparation of the high efficiency column which has not been constructed up to now is realized.

The new high pressure sealing mechanism provides for the direct connection of two columns, leading to the construction of a multi-column system with a small dead volume.

As the most convenient feature of this system, the simplicity of the sealing mechanism should be stressed. When the column fitting plug is inserted into the end of the glass column tube, and is fitted by the clips, the column is ready to use. The procedure is very simple and easy.

The end fitting plug is interchangeable in all columns which, regardless of their interdiameter and volume, have the uniform column end syringe. A single column-end fitting plug is usable for constructing various sizes of high pressure glass columns.

EXAMPLE 1

A high pressure glass column for high performance liquid chromatograph (wall thickness 2.5 mm, inner diameter 4 mm and length 30 cm) which was fitted with glass flanges on both ends made by the same glass material was used.

A column fitting plug was inserted into the lower end of the high pressure glass tube and a filter was placed on it. The plug and filter (pore diameter 5 micron) were made of polytetrafluoroethylene (PTFE). Inside of the glass tube, spherical silica gel-ODS (particle size 10 micron, Wakogel LCK-ODS-10, Wako Pure Chemicals Company) was packed by the conventional slurry packing procedure. A filter was placed over the column bed and then a fitting plug was inserted over the filter. The filter and the fitting plug were made of PTFE in the same manner as the above. The flanges of both column ends were attached by the fitting plugs and were kept together by using clips. The column was connected by the high pressure liquid chromatography.

Methanol/water (1:2 v/v) was pumped through the bore into the column. Flow rate was 0.5 ml/min. The pressure of the column head was 60 kg/cm$^2$. The flow was continued for several days and no leak of the effluent was observed.

Figure 5:
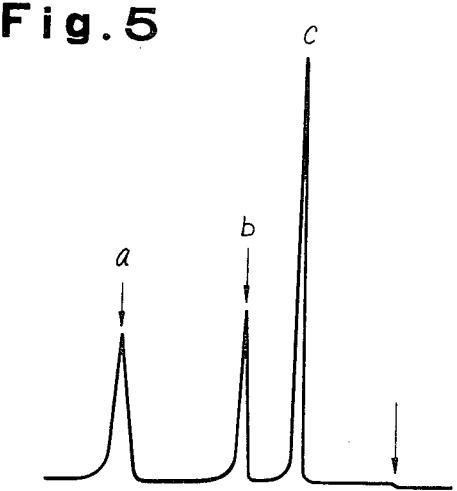
FIGS. 5 and 6 show the chromatograms provided by using the glass column system described in this invention.

The septum injector was connected with the bore of the column and the mixture of methyl, ethyl, n-propyl p-hydroxybenzoates dissolved in the mobile phase solvent was injected by using a stop-flow procedure. The chromatogram obtained was shown in FIG. 5. In FIG. 5, $a$, $b$ and $c$ shows propyl ester, ethyl ester and methyl ester, respectively.

EXAMPLE 2

The high pressure glass column for high performance liquid chromatograph (wall thickness 3 mm, inner diameter 10 mm and length 30 cm) was conically narrowed in inner diameter (4 mm) at both ends of the glass column as shown in FIG. 2.

Inside of the glass tube, spherical silica (particle size 10 micron, Wakogel LCH-10) was packed by the conventional slurry packing procedure.

Figure 6:

Eluent was n-hexane/ethyl acetate (9:1 v/v). Flow rate was 2 ml/min. The sample mixture containing di-Me, di-Et, di-Bu phthalates in the mobile phase solvent was injected into the column. The pressure of the column head was 30 kg/cm. The chromatogram obtained was shown in FIG. 6. In FIG. 6, $d$, $e$ and $f$ show dimethyl ester, diethyl ester and dibutyl ester, respectively. The theoretical plate number of the dimethyl phthalate, calculated from the chromatogram, was 10,000/meter.

What is claimed is:

1. In a high pressure glass column for liquid chromatography, a high pressure glass column for high performance liquid chromatography which comprises:
    (a) a glass column having at each end thereof a flange made of the same material as said column, said each end communicating via a conical passage with a shorter column of smaller diameter and in which a chromatographic absorbent is packed;
    (b) a distributing filter made of a fluoropolymeric resin fitted in each said shorter column and tightly packed against said absorbent;
    (c) a fitting plug made of the same material as the filter, said plug having an external annular flange at the center portion thereof, one end of which is extended beyond the end of the shorter column and the other end of which is packed into the shorter column and contacts one said filter so that the outer face of each said fitting plug tightly contacts the inner face of the shorter column, wherein each said plug includes a small diameter axial bore and the outlet thereof is formed in a bowl-like shape, and a plurality of hollows are circumferentially formed in the plug above the bowl so that the mouth of the bowl may be enlarged to compress against the inside of the column tube and the hollows may be shrunk by the enlargement of the bowl; and
    (d) a clip fitting and holding the two flanges of the main column and the plug.

2. The high pressure glass column for high performance liquid chromatograph claimed in claim 1 wherein the ends of the high pressure glass column are 4 to 30 mm in inner diameter.

3. The high pressure glass column for high performance liquid chromatograph claimed in claim 1 wherein the inner diameter of the ends are reduced to form small syringe tubes having inner diameters of 4 to 30 mm.

4. The high pressure glass column for high performance liquid chromatograph claimed in claim 3 wherein the inner diameter of both ends are reduced to to form small syringe tubes having inner diameters of 4 to 10 mm.

5. The high pressure glass column for high performance liquid chromatograph cliamed in claim 1, wherein the filter and the fitting plug are made of at least one fluorine-contained resin.

* * * * *